United States Patent
Zemenchik et al.

(10) Patent No.: US 10,028,424 B2
(45) Date of Patent: Jul. 24, 2018

(54) SYSTEM FOR MOUNTING AN AGRICULTURAL SOIL ANALYZER TO AGRICULTURAL IMPLEMENT

(71) Applicant: CNH Industrial America LLC, New Holland, PA (US)

(72) Inventors: Robert A. Zemenchik, Kenosha, WI (US); Matthew Huenemann, Racine, WI (US)

(73) Assignee: CNH Industrial America LLC, New Holland, PA (US)

( * ) Notice: Subject to any disclaimer, the term of this patent is extended or adjusted under 35 U.S.C. 154(b) by 483 days.

(21) Appl. No.: 14/695,945

(22) Filed: Apr. 24, 2015

(65) Prior Publication Data

US 2015/0305227 A1 Oct. 29, 2015

Related U.S. Application Data

(60) Provisional application No. 61/984,471, filed on Apr. 25, 2014.

(51) Int. Cl.
*A01B 79/00* (2006.01)
*A01B 71/02* (2006.01)
(Continued)

(52) U.S. Cl.
CPC .......... *A01B 79/005* (2013.01); *A01B 63/32* (2013.01); *A01B 67/00* (2013.01); *A01B 71/02* (2013.01);
(Continued)

(58) Field of Classification Search
CPC ....... A01B 79/005; A01B 63/32; A01B 67/00; A01B 71/02; A01B 76/00; A01C 7/102;
(Continued)

(56) References Cited

U.S. PATENT DOCUMENTS

| 4,674,578 A | 6/1987 | Bexten et al. |
| 5,033,397 A | 7/1991 | Colburn, Jr. |

(Continued)

FOREIGN PATENT DOCUMENTS

| CN | 202421071 U | 9/2012 |
| EP | 0615682 A1 | 9/1994 |

(Continued)

OTHER PUBLICATIONS

Sattler, Claudia, Teilflachenspezifische Bewirtschaftung, Ein Konzept zur Integration Von Umwelt-und Naturschutzzielen in die Nutzung landwirtschaftlicher Produktionsflachen, Feb. 1, 2002, pp. 1-4.

(Continued)

*Primary Examiner* — Lisa Caputo
*Assistant Examiner* — Nathaniel T Woodward
(74) *Attorney, Agent, or Firm* — Rebecca L. Henkel; Rickard K. DeMille

(57) ABSTRACT

A system includes a retractable mounting assembly including a frame assembly. The frame assembly includes at least one substantially rigid frame member. In some embodiments, the frame assembly is configured to facilitate movement of an agricultural soil analyzer from a first position longitudinally proximate to a rear end of an agricultural implement to a second position longitudinally rearward of the first position, relative to a direction of travel of the agricultural implement, the frame assembly is configured to position the agricultural soil analyzer above a surface of an agricultural field while in the second position, and each of the at least one substantially rigid frame member is formed from a non-electrically interactive material.

20 Claims, 7 Drawing Sheets

(51) Int. Cl.

| | |
|---|---|
| *A01C 7/10* | (2006.01) |
| *A01C 21/00* | (2006.01) |
| *A01B 76/00* | (2006.01) |
| *G01N 27/02* | (2006.01) |
| *G01N 33/24* | (2006.01) |
| *A01B 63/32* | (2006.01) |
| *A01B 67/00* | (2006.01) |
| *A01G 25/16* | (2006.01) |
| *G01V 3/15* | (2006.01) |

(52) U.S. Cl.
CPC .............. *A01B 76/00* (2013.01); *A01C 7/102* (2013.01); *A01C 21/005* (2013.01); *G01N 27/028* (2013.01); *G01N 33/24* (2013.01); *A01G 25/167* (2013.01); *G01N 2033/245* (2013.01); *G01V 3/15* (2013.01); *Y02P 60/214* (2015.11)

(58) Field of Classification Search
CPC .... A01C 21/005; G01N 27/028; G01N 22/24; G01N 2033/245; G01N 1/04; G01N 33/24; Y02P 60/214; A01G 25/167; G01V 3/15; G06F 19/00
See application file for complete search history.

(56) References Cited

U.S. PATENT DOCUMENTS

| | | | |
|---|---|---|---|
| 5,394,949 A | 3/1995 | Wright et al. | |
| 5,425,427 A | 6/1995 | Haugen | |
| 5,479,992 A | 1/1996 | Bassett | |
| 5,524,560 A | 6/1996 | Carter | |
| 5,663,649 A | 9/1997 | Topp et al. | |
| 6,016,713 A | 1/2000 | Hale | |
| 6,041,582 A | 3/2000 | Tiede et al. | |
| 6,608,672 B1 | 8/2003 | Shibusawa et al. | |
| 6,937,939 B1 | 8/2005 | Shibusawa et al. | |
| 7,068,051 B2 | 6/2006 | Anderson | |
| 7,216,555 B2 | 5/2007 | Drummond et al. | |
| 7,254,485 B2 | 8/2007 | Rooney et al. | |
| 8,011,439 B2 | 9/2011 | Gadzella et al. | |
| 8,204,689 B2 | 6/2012 | Christy et al. | |
| 8,451,449 B2 | 5/2013 | Holland | |
| 8,768,667 B2 | 7/2014 | Lindores | |
| 2002/0169558 A1* | 11/2002 | Smith ...................... | G01V 3/15 702/5 |
| 2005/0172733 A1* | 8/2005 | Drummond .......... | A01B 79/005 73/864.41 |
| 2008/0047475 A1 | 2/2008 | Stehling et al. | |
| 2010/0283603 A1 | 11/2010 | Yule et al. | |
| 2011/0153168 A1 | 6/2011 | Peterson et al. | |
| 2011/0153169 A1 | 6/2011 | Peterson | |
| 2012/0227992 A1 | 9/2012 | Henry | |
| 2013/0184944 A1 | 7/2013 | Missotten et al. | |
| 2013/0233088 A1 | 9/2013 | Noble et al. | |
| 2014/0048001 A1 | 2/2014 | Bassett | |
| 2014/0048296 A1 | 2/2014 | Bassett | |

FOREIGN PATENT DOCUMENTS

| | | |
|---|---|---|
| EP | 1241488 A2 | 9/2002 |
| EP | 2586634 A1 | 5/2013 |
| JP | S6474912 | 3/1989 |
| WO | 02/49414 A1 | 6/2002 |
| WO | 2013131882 A2 | 9/2013 |

OTHER PUBLICATIONS

Scholderle, Florian et al., Multi Sensor System Requirements for a Position Steered Seed Deposition in Sugar Beet Cultivation for the Generation of a Rectangular Formation, Jan. 1, 2008, pp. 1-11.
Grisso, Robert et al., Precision Farming Tools: Variable-Rate Application, Virginia Cooperative Extension, Jan. 1, 2011, pp. 1-16.
Koch, Julia, Schlaue Schlepper, Agraringenieure Entwickeln den Traktor der Zukunft: Mit Hilfe von Satelliten und Hightech-Sensoren Soll er Kunftig Jedes Pflanzchen Personlich Umsorgen, Technik, Aug. 23, 2010, p. 133.
International Search Report and Written Opinion for International Application No. PCT/US2015/027617 dated Jul. 23, 2015.
International Search Report and Written Opinion for International Application No. PCT/US2015/027602 dated Jul. 3, 2015.
International Search Report and Written Opinion for International Application No. PCT/US2015/027629 dated Jul. 23, 2015.
Adamchuk, Viacheslav I.; Precision Agriculture: Does It Make Sense?; Better Crops/vol. 94 (2010, No. 3);pp. 4-6; http://www.ipni.net/publication/bettercrops.nsf/0/DD1B3874E030BC1485257980006039BF/$File/Better%20Crops%202010-3%20p4-6.pdf; accessed Jul. 20, 2015.
Adamchuk, Viacheslav I.; On-the-Go Proximal Soil Sensing for Agriculture; Feb. 21, 2011; http://adamchukpa.mcgill.ca/presentations/Agri-Sensing_2011.pdf; accessed Jul. 20, 2015.
Gunzenhauser, Bob; Shanahan, John; and Lund, Eric; Crop Insights: Utilizing On-the Go Soil Sensing Devices to Improve Definition of Management Zones; https://www.pioneer.com/home/site/us/agronomy/soil-sensing-mgmt-zones/; accessed Jul. 20, 2015.
Grift, Tony E.; Kasten, Matthias; and Nagasaka, Yoshida; Development of Autonomous Robots for Agricultural Applications; http://abe-research.illinois.edu/faculty/grift/research/biosystemsautomation/agrobots/RoboticsUIUC_CropProtectionConf.pdf; accessed Jul. 20, 2015.
University of Nebraska-Lincoln; Soil Sensing; CropWatch; 2014; http://cropwatch.unl.edu/ssm/sensing; accessed Jul. 20, 2015.
Dualem-21S; http://www.dualem.com/products.html; accessed Jul. 20, 2015.
Geonics EM38-MK2 Ground Conductivity Meter; 2013; http://www.geonics.com/html/em38.html; accessed Jul. 20, 2015.
Reese Towpower One Wrench Tightening System; http://www.cequentconsumerproducts.com/_literature_104080/Interlok_-_One_Wrench_Tightening_System; accessed Jul. 21, 2015.
Adamchuk, Viacheslav I.; Hummel, J.W.; Morgan, M.T.; and Upadhyaya, S. K.; On-the-go Soil Sensors for Precision Agriculture; Biological Systems Engineering: Papers and Publication, University of Nebraska-Lincoln; Jun. 14, 2004.
Knight, Quenten; Electromagnetic Soil Mapping—Implementing the Outcomes; 5th Australian Controlled Traffic and Precision Agriculture Conference, University of Western Australia; Jul. 16-18, 2007; pp. 89-97.
U.S. Appl. No. 14/695,454, filed Apr. 24, 2015, Robert A. Zemenchik.
U.S. Appl. No. 14/695,753, filed Apr. 24, 2015, Robert A. Zemenchik.

* cited by examiner

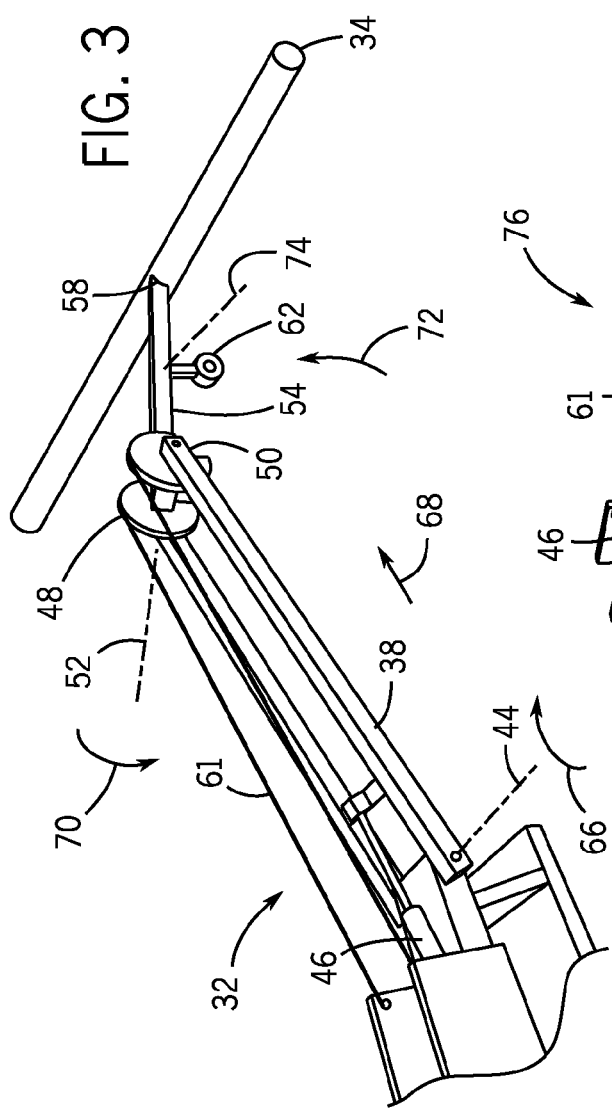
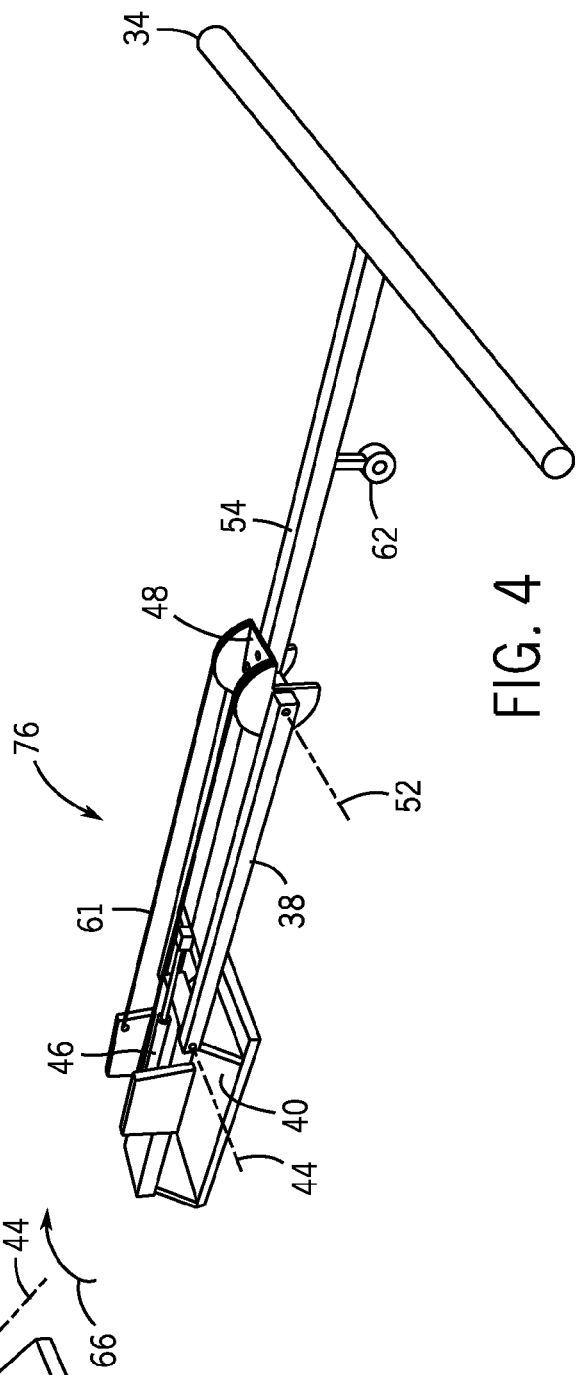

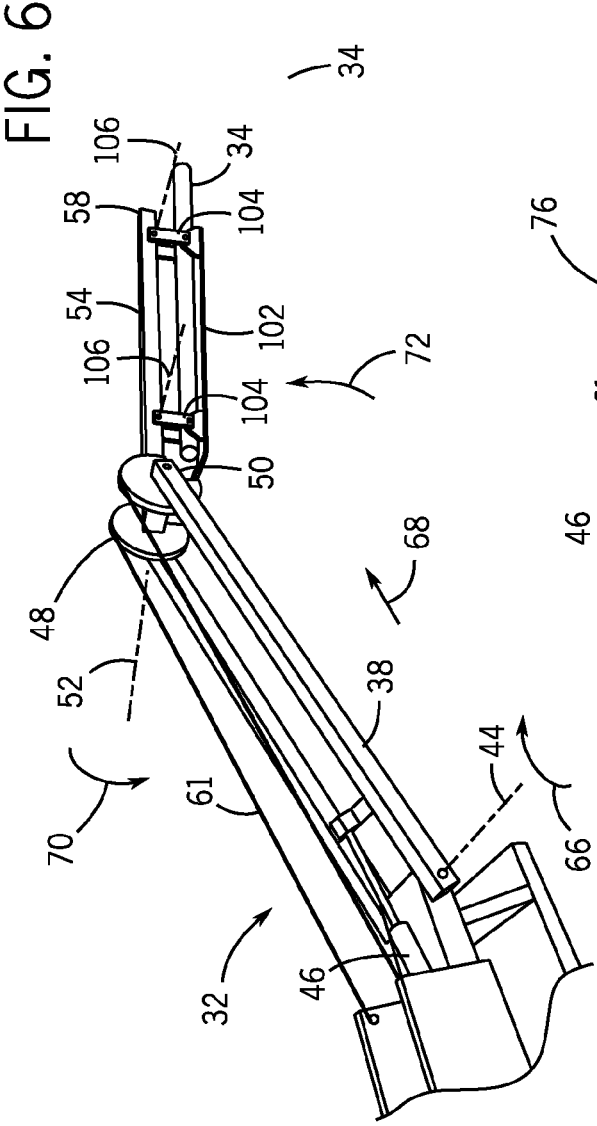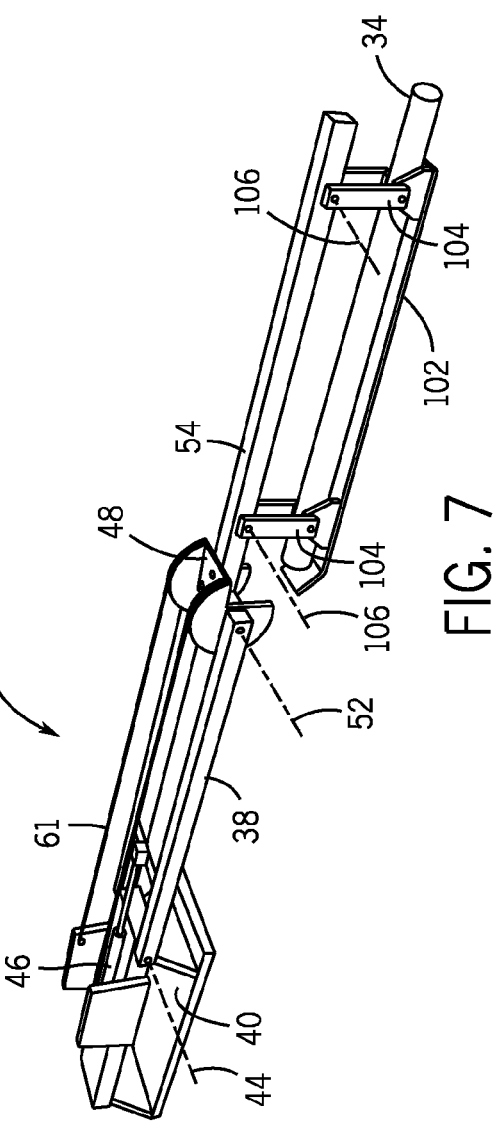

SYSTEM FOR MOUNTING AN AGRICULTURAL SOIL ANALYZER TO AGRICULTURAL IMPLEMENT

CROSS-REFERENCE TO RELATED APPLICATIONS

This application claims priority from and the benefit of U.S. Provisional Application Ser. No. 61/984,471, entitled "SYSTEM FOR MOUNTING AN AGRICULTURAL SOIL ANALYZER TO AGRICULTURAL IMPLEMENT," filed Apr. 25, 2014, which is hereby incorporated by reference in its entirety.

BACKGROUND

The invention relates generally to agricultural systems and, more particularly, to a mounted assembly for an agricultural soil analyzer.

Certain agricultural operators may conduct soil analysis before beginning planting operations in agricultural fields. Soil analysis can assist in planning planting operations to increase yield or planting efficiency. For example, an analysis that indicates a high clay content may influence application of fertilizer or seeding operations in specific areas. Ultimately, operators may reduce waste and save time by limiting planting in undesirable areas of agricultural fields. Moreover, unwanted compaction of the soil may be reduced by performing fewer passes in the agricultural field. However, typical soil analysis may be time consuming, expensive, and data intensive.

BRIEF DESCRIPTION

In one embodiment, a retractable mounting assembly includes a frame assembly. The frame assembly includes at least one substantially rigid frame member. In some embodiments, the frame assembly is configured to facilitate movement of an agricultural soil analyzer from a first position longitudinally proximate to a rear end of an agricultural implement to a second position longitudinally rearward of the first position, relative to a direction of travel of the agricultural implement, the frame assembly is configured to position the agricultural soil analyzer above and proximate to a surface of an agricultural field while in the second position, and each of the at least one substantially rigid frame member is formed from a non-electrically interactive material.

In another embodiment, a mounting assembly for an agricultural soil analyzer includes a first support arm. The first support arm is configured to rotatably couple to an agricultural implement. In some embodiments, the first support arm is configured to rotate about a first axis between a stored position configured to position the agricultural soil analyzer longitudinally proximate to a rear end of the agricultural implement and an operation position configured to position the agricultural soil analyzer above and proximate to a surface of an agricultural field and longitudinally rearward of the rear end of the agricultural implement relative to a direction of travel of the agricultural implement. In some embodiments, the first support arm is formed from a substantially rigid non-electrically interactive material.

In another embodiment, an agricultural soil analysis system includes a non-contact electrical conductivity probe. The non-contact electrical conductivity probe is configured to measure electrical conductivity of soil in an agricultural field. The system also includes a mounting assembly. In some embodiments, the mounting assembly includes a frame assembly coupled to the non-contact electrical conductivity probe and configured to couple to a rear end of an agricultural implement. The frame assembly includes at least one substantially rigid frame member, and each of the at least one substantially rigid frame members is formed from a non-electrically interactive material. The system includes an interface module communicatively coupled to the agricultural soil analyzer and configured to communicatively couple to a control system of the agricultural implement.

DRAWINGS

These and other features, aspects, and advantages of the present invention will become better understood when the following detailed description is read with reference to the accompanying drawings in which like characters represent like parts throughout the drawings, wherein:

FIG. 3 is a perspective view of the mounting assembly of FIG. 2, in which the mounting assembly is positioned between a stored position and an operation position;

FIG. 4 is a perspective view of the mounting assembly of FIG. 2, in which the mounting assembly is positioned in the operation position;

FIG. 6 is a perspective view of the mounting assembly of FIG. 5, in which the mounting assembly is positioned between a stored position and an operation position;

FIG. 7 is a perspective view of the mounting assembly of FIG. 5, in which the mounting assembly is positioned in the operation position;

DETAILED DESCRIPTION

Figure 1:
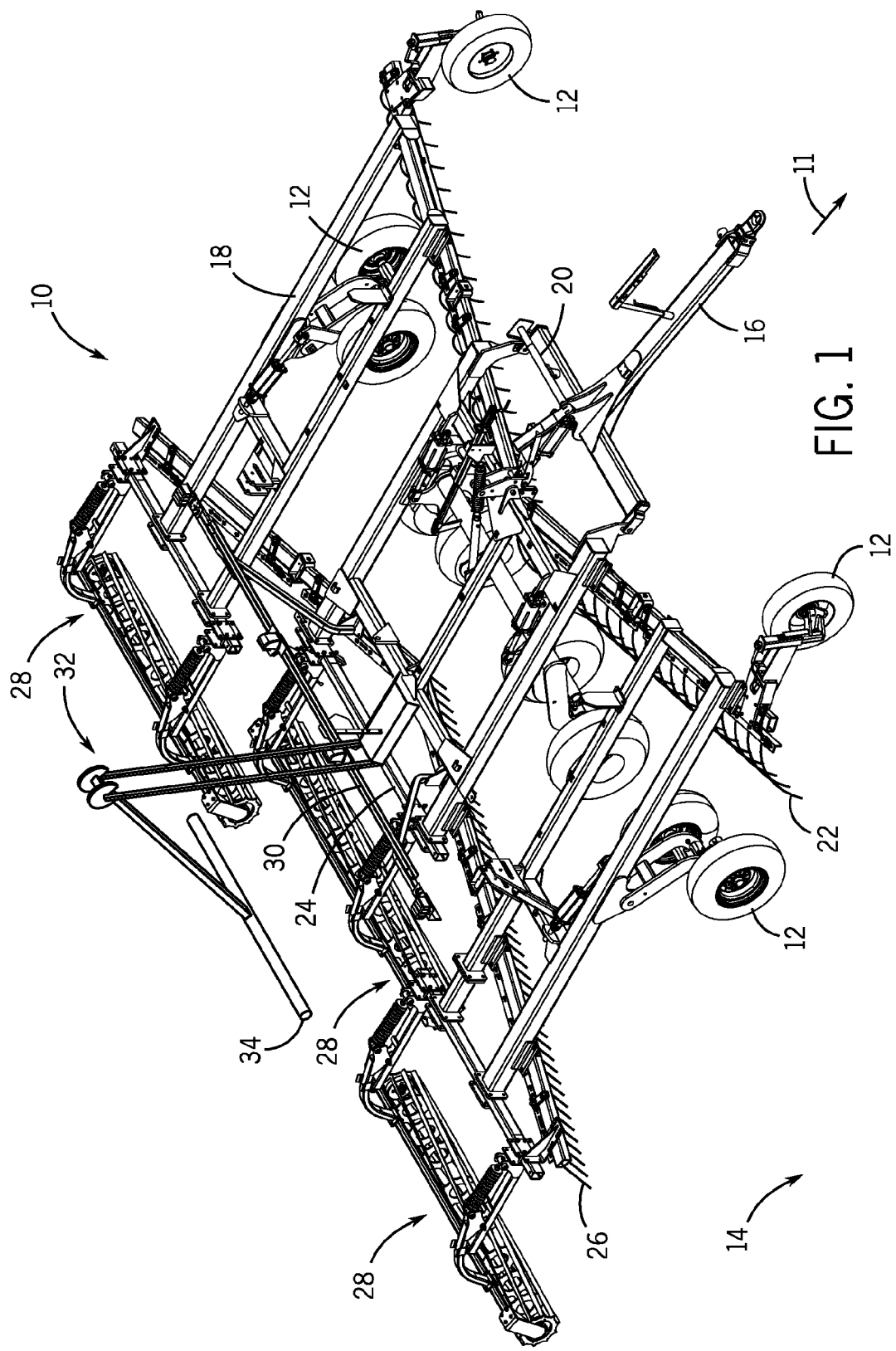
FIG. 1 is a perspective view of an embodiment of an agricultural implement, including an agricultural soil analyzer mounting assembly.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments.

The embodiments described herein relate to a system for mounting and deploying an agricultural soil analyzer for monitoring an agricultural field. In particular, a system for mounting the analyzer on a soil conditioning implement and obtaining data is disclosed. For example, in certain embodiments, a mounting assembly includes frame assembly having a first support arm coupled to second support arm. The second support arm is configured to rotate about a second axis. In some embodiments, the mounting assembly includes actuators configured to drive the first support arm to rotate about a first axis and to drive the second support arm to rotate about the second axis. For example, while the mounting assembly is in a stored position, the actuator may be retracted such that the frame assembly is substantially perpendicular to the agricultural field. That is, the agricultural soil analyzer coupled to the second support arm is longitudinally proximate to a rear end of the agricultural implement. However, the actuator is configured to drive the mounting assembly to an operation position in which the frame assembly is substantially parallel to the agricultural field. Similarly, a second actuator is configured to drive the second support arm to the operation person in which the second support arm is substantially parallel to the agricultural field. In other words, the frame assembly positions the agricultural soil analyzer longitudinally rearward of the stored position, described above, relative to a direction of travel of the agricultural implement. Moreover, the agricultural soil analyzer is positioned above the surface of the agricultural field. In certain embodiments, the second actuator may include a cable or band extending between the implement and the second support arm. Moreover, the second support arm is collapsible and configured to extend away from the agricultural implement, thereby separating the analyzer from ferrous and/electrically interactive components of the agricultural implement. In certain embodiments, a support wheel supports the weight of the frame assembly and analyzer when the mounting assembly is in the operation position. In other embodiments, a sled may support the weight of the frame assembly and analyzer when the mounting assembly is in the operation position. In certain embodiments, the analyzer is coupled to the support arm. The second support arm is configured to hold the analyzer proximate to the agricultural field while in the operation position to enable the analyzer to obtain measurements from the agricultural field. For example, the analyzer may transmit and receive electromagnetic energy to and/or from the agricultural field. Data acquired by the analyzer may be directed to a wireless transmitter for storage in a remote server. The data may be used to generate three dimensional soil maps to direct planting operations.

Soil analysis may be conducted in a variety of ways. For example, soil samples may be removed from the agricultural field and analyzed in a laboratory setting. Additionally, non-contact and/or soil surface sensors may be used to obtain various soil properties while reducing disturbance of the agricultural field. Typically, when using non-contact sensors, operators conduct soil analysis separately from planting, fertilizing, and/or tillage operations. For example, one pass may be used to conduct soil analysis, in which the operator tows equipment over the agricultural field to obtain data for evaluation. The data may then be evaluated to generate soil maps or yield maps indicating a variety of field properties. The soil maps may be used to direct future planting, fertilizing, and/or tillage operations. Then, subsequent passes may be used to condition the soil, fertilize the soil, and/or deposit seeds in the soil. During the fertilizing and/or planting process, the operator may consult the soil maps to adjust fertilizer rates and/or planting rates based on the properties obtained from the soil analysis. Using multiple passes increases the cost and the time it takes for operators to condition, fertilize, and plant the field. Combing the conditioning and soil analysis process eliminates at least one field pass that operators may make when preparing fields for planting. Moreover, by conducting soil analysis closer to actual planting operations, operators have better data related to current soil conditions, such as salinity, cation exchange capacity, clay content, or the like. As a result, efficiency may be increased, along with yields.

Turning now to the drawings, and referring first to FIG. 1, a perspective view of an embodiment of an agricultural implement 10 is illustrated in the form of a soil conditioner. However, in alternative embodiments, the agricultural implement 10 may be a field cultivator, a fertilizer applicator, a planter, or the like. The implement 10 is configured to be towed behind a work vehicle, such as a tractor, in a direction of travel 11. The implement 10 includes wheels 12 which are used to guide the implement 10 along an agricultural field 14. The implement 10 is attached to the tractor via a hitch assembly 16. In certain embodiments, the hitch assembly 16 is connected via bolts or other suitable couplings to an implement frame 18. The implement frame 18 includes a front tool bar 20 coupled to a plurality of blades 22, in the illustrated embodiment. The blades 22 are configured to contact the agricultural field 14 to break up the soil and prepare the agricultural field 14 for planting. The structural members of the agricultural implement 10, such as the frame 18 and the hitch assembly 16, may be made of any suitable material, such as structural steel. In addition, the implement frame 18 includes a rear tool bar 24. The rear tool bar 24 is coupled to leveling bars 26, in the illustrated embodiment. The leveling bars 26 are configured to smooth the surface of the agricultural field 14 in preparation for planting. Further, the implement 10 includes rolling baskets 28. The rolling baskets 28 are configured to condition the soil in preparation for planting.

In the illustrated embodiment, the agricultural implement 10 includes a rear hitch 30 coupled to the frame 18. Furthermore, a mounting assembly 32 (e.g., mounting soil sampling assembly) is coupled to the rear hitch 30. The mounting assembly 32 may be attached to the rear hitch 30 using any suitable connector (e.g., pins, bolts, etc.). The mounting assembly 32 is configured to support an agricultural soil analyzer 34 (e.g., probe, meter, detector, analyzer, etc.). In the illustrated embodiment, the analyzer 34 is an electrical conductivity probe configured to operate via electromagnetic induction to determine conductivity, susceptibility, thickness and/or the like of the agricultural field 14. By using an electrical conductivity probe as the analyzer 34, disturbance to the soil may be reduced while obtaining relatively quick analysis. In some embodiments, the analyzer 34 includes multiple receivers and transmitters to obtain information about the agricultural field 14. As will be discussed below, the information obtained by the analyzer 34 may be used to generate two- or three-dimensional soil maps of the agricultural field to enhance planting operations. However, as mentioned above, other analyzers 34 may be used in other embodiments. In certain embodiments, the analyzer 34 is a non-contact (e.g., soil surface sensor; low disruption or compaction sensor, etc.) analyzer that is configured to be positioned proximate to and above the agricultural field 14 while obtaining data. As used herein, proximate refers to a distance that enables the analyzer 34 to obtain accurate readings without significantly disrupting or compacting the surface of the agricultural field 34. For example, in some embodiments, the analyzer 34 may be 6 inches, 12 inches, 24 inches, or 36 inches, among other distances, from the surface of the agricultural field 14. Moreover, as discussed in detail below, the analyzer 34 may be integrated with other electronic components or systems including a global positioning system (GPS), engine controls, data acquisition software, and the like.

As will be described in detail below, the mounting assembly 32 is configured to extend and retract between a first position and a second position. In the illustrated embodiment, the analyzer 34 is longitudinally proximate to the rear end of the agricultural implement 10 while in the first position. However, while in second position the analyzer 34 is positioned longitudinally rearward of the first position, relative to the direction of travel 11 of the implement 10. Moreover, the analyzer 34 is positioned proximate to the surface of the agricultural field 14. Moreover, the mounting assembly 32 and/or components of the mounting assembly 32 are formed from non-electrically interactive material in the illustrated embodiment. As a result, the analyzer 34 is separated from the ferrous and/or metallic components of the agricultural implement 10.

Figure 2:
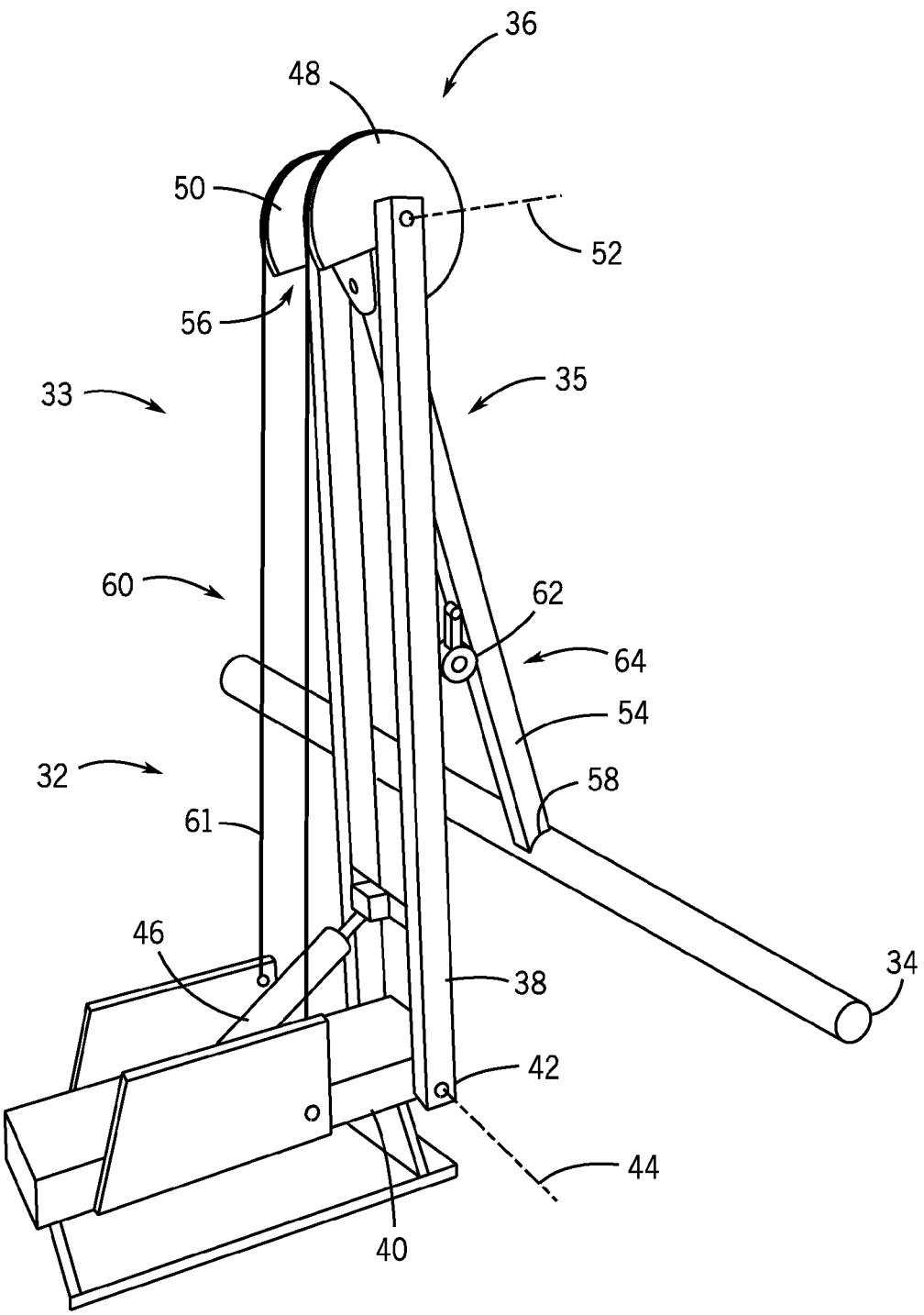
FIG. 2 is a perspective view of an embodiment of a mounting assembly that may be employed to adjust a position of an agricultural soil analyzer.

FIG. 2 is a perspective view of the mounting assembly 32 in a stored position 36. As will be described in detail below, the mounting assembly 32 is foldable or collapsible and configured to position the analyzer 34 proximate to the surface of the agricultural field 14. The mounting assembly 32 includes a frame assembly 33. Moreover, the frame assembly 33 includes substantially rigid frame members 35, as described in detail below. In the stored position 36, the analyzer 34 is deactivated. That is, data acquisition does not begin until the analyzer 34 is proximate to the surface of the agricultural field 14. Moreover, a first support arm 38 (e.g., frame member 35) of the mounting assembly 32 is substantially perpendicular to the agricultural field 14 while the mounting assembly 32 is in the stored position 36. As shown, the first support arm 38 is rotatably coupled to the rear hitch 30 at a base 40. The base 40 is configured to secure the mounting assembly 32 to the rear hitch 30 or any other suitable location at the rear end of the implement 10. In the illustrated embodiment, the first support arm 38 is coupled to the base 40 at a first end 42 of the first support arm 38. As mentioned above, the mounting assembly 32 is in the stored position 36 in FIG. 2. As a result, the first support arm 38 is in a substantially vertical orientation relative to the ground. However, the first support arm 38 is configured to rotate about a first axis 44. As discussed in detail below, rotation of the first support arm 38 about the first axis 44 transitions the mounting assembly 32 between the stored position 36 and an operation position in which the analyzer 34 is positioned rearward of the implement 10 and proximate to the soil surface.

As mentioned above, the first support arm 38 rotates about the first axis 44 to transition the assembly 32 between the stored position 36 and an operation position. In the illustrated embodiment, an actuator 46 drives the first support arm 38 to rotate about the first axis 44. As shown, the actuator 46 is a hydraulic cylinder configured to extend and retract a piston coupled to the first support arm 38 to drive rotation about the first axis 44. For example, when the piston is retracted the first support arm 38 is driven toward the stored position of the assembly 32 and when the piston is extended the first support arm 38 is driven toward the operation position of the assembly 32. However, it should be appreciated that alternative linear actuators (e.g., screw drives, electromechanical actuators, etc.) may be employed in alternative embodiments. In further embodiments, a rotary actuator (e.g., hydraulic, electrical, etc.) may be used. In certain embodiments, a gear and pulley system may be utilized to drive rotation of the first support arm 38. Moreover, as will be discussed in detail below, a control system may be included to control operation of the actuator 46.

The mounting assembly 32 also includes a rotation member 48 rotatably coupled to the first support arm 38 at a second end 50. In the illustrated embodiment, the rotation member 48 is configured to rotate about a second axis 52. Moreover, the rotation member 48 is coupled to a second support arm 54 at a first end 56 of the second support arm 54. The second support arm 54 is configured to rotate about the second axis 52 relative to the rotation of the first support arm 38. That is, the second support arm 54 rotates about the second axis 52 with the rotation member 48. The second support arm 54 is configured to support the analyzer 34 at a second end 58 of the second support arm 54. As a result, the analyzer 34 is moved toward the position rearward of the implement and proximate to the soil surface as the first support arm 38 and the second support arm 54 are moved to the operation position.

In the illustrated embodiment, an actuator 60 drives the second support arm 54 to rotate about the second axis 52. As shown, the actuator 60 includes cables 61 extending from the base 40 to the rotation member 48. The cables 61 drives the rotation member 48 to rotate about the second axis 52 as the first support arm 38 rotates about the first axis 44. That is, tension in the cables 61 increases as the first support arm 38 rotates about the first axis 44, and that tension is applied to the rotation member 48 to drive the rotation member 48 to rotate about the second axis 52. As a result, the second support arm 54 also rotates about the second axis 52. The cables 61 are formed from non-electrically interactive material in the illustrated embodiment, as described in detail below. However, in alternative embodiments, the cables 61 may be straps, ropes, or any material capable of applying force to the rotation member 48 and/or second support arm 54.

In the illustrated embodiment, a support wheel 62 is rotatably coupled to the second support arm 54. The support wheel 62 is positioned on the second support arm 54 such that the support wheel 62 is in a retracted position 64 while the mounting assembly 32 is in the stored position 36 and in a lowered position while the mounting assembly 32 is in the operation position. Accordingly, the position of the support wheel 62 corresponds to the position of the second support arm 54. As discussed below, the support wheel 62 is configured to distribute the weight of the second support arm 54 and the analyzer 34 while the mounting assembly 32 is in the operation position. Moreover, the support wheel 62 is sized to place the analyzer 34 proximate to the surface of the agricultural field 14 while the mounting assembly 32 is in the operation position. As a result, the support wheel 62 enables the analyzer 34 to monitor the soil without contacting the surface of the agricultural field 14. Moreover, the support wheel 62 distributes the weight of the second support arm 54 and actuator 46, allowing for longer lengths of the first support arm 38 and second support arm 54. It is appreciated that while one support wheel 62 is shown in the illustrated embodiment, the second support arm 54 and/or the first support arm 38 may include several support wheels 62 in alternative embodiments. Moreover, in the illustrated embodiment, the support wheel 62 is formed from a non-electrically interactive material.

The mounting assembly 32 and/or the associated components are constructed from non-electrically interactive materials in the illustrated embodiment. As used herein, non-electrically interactive material refers to materials that substantially do not interfere or influence surrounding electric fields. For example, the mounting assembly 32 may be assembled from components formed from a thermoplastic, fiber reinforced polymer, or composite material. Moreover, non-electrically interactive may refer to materials that are non-electrically conductive or substantially non-electrically conductive. As will be discussed in detail below, constructing the mounting assembly 32 from a non-electrically interactive material may improve the performance of the analyzer 34. That is, a non-electrically interactive material substantially reduces interference from the mounting assembly 32, thereby enhancing the accuracy of the agricultural soil analyzer 34. However, in certain embodiments, only part of the mounting assembly 32 is constructed from non-electrically interactive materials. For example, the base 40 may be formed from a metallic material.

FIG. 3 is a perspective view of the mounting assembly 32 in an intermediate position between the stored position 36 and the operation position. In the illustrated embodiment, the first support arm 38 rotates about the first axis 44, via the actuator 46, in a first direction 66, thereby moving the second end 50 of the first support arm 38 in a longitudinal direction 68 that is opposite the direction of travel 11 of the agricultural implement 10. As the first support arm 38 rotates about the first axis 44, the second end 50 of the first support arm 38 is moved closer to the surface of the agricultural field 14. Moreover, in the illustrated embodiment, the second support arm 54 is driven to rotate about the second axis 52 in a second direction 70 by the actuator 60 (e.g., cables 61). As shown, the second direction 70 is opposite the first direction. Accordingly, rotation in the second direction 70 drives the second end 58 of the second support arm 54 to move in the direction 68. As a result, the mounting assembly 32 is elongated as the mounting assembly 32 transitions to the operation position, thereby moving the agricultural soil analyzer 34 rearwardly.

As mentioned above, the second support arm 54 includes the support wheel 62 configured to transition between the retracted position 64 while the mounting assembly 32 is in the stored position 36 and a lowered position 72 while the mounting assembly 32 is in the operation position. In the illustrated embodiment, the support wheel 62 is rotated about a wheel axis 74 as the second support arm 54 rotates about the second axis 52 in the second direction 70. The support wheel 62 is mounted to the second support arm 54 such that gravity pulls the support wheel to the lowered position 72 as the mounting assembly 32 transitions to the operation position. Additionally, the support wheel 62 rotates back to the retracted position 64 as the mounting assembly 32 transitions toward the stored position 36.

FIG. 4 is a perspective view of the mounting assembly 32 in an operation position 76. As described above, the first support arm 38 is driven about the first axis 44 in the first direction 66 by the actuator 46. In the operation position 76, the first support arm 38 is substantially parallel to the surface of the agricultural field 14. Moreover, the second support arm 54 is driven about the second axis 52 in the second direction 70 by the actuator 60. As a result, the second support arm 54 is oriented substantially parallel to the surface of the agricultural field 14. Furthermore, the support wheel 62 contacts the surface of the agricultural field 14 to support the weight of the mounting assembly 32 in the operation position 76.

As shown, in the illustrated embodiment, the analyzer 34 is proximate to the surface of the agricultural field 14 while the mounting assembly 32 is in the operation position 76. As a result, the analyzer 34 is positioned to emit and/or receive electromagnetic energy into/from the soil without contacting the surface of the agricultural field 14. Furthermore, in the illustrated embodiment, the mounting assembly 32 extends in the direction 68. As illustrated, the mounting assembly 32 extends from the rear end of the implement 10 in a rearward direction relative to the direction of travel 11 of the implement 10. The extension of the mounting assembly 32 is configured to longitudinally separate the analyzer 34 from the ferrous and/or electrically interactive components of the agricultural implement 10, thereby enabling the analyzer 34 to obtain readings with improved precision due to reduced interference from the electrically interactive components. In the illustrated embodiment, the analyzer 34 is positioned approximately 8 feet rearward of the agricultural implement 10 relative to the direction of travel 11. However, in other embodiments, the analyzer 34 may be farther or closer. For example, the mounting assembly 32 may position the analyzer 34 may be between 5 feet and 20 feet from the agricultural implement 10. Moreover, additional support wheels 62 may be coupled to the first support arm 38 and/or the second support arm 54 to support the mounting assembly 32 in embodiments having assemblies that extend farther distances from the agricultural implement 10. Furthermore, multiple mounting assemblies 32 and analyzers 34 may be coupled to the agricultural implement 10. For example, mounting assemblies 32 may be mounted across the rear end of the agricultural implement 10 such that the analyzers 34 span the length of the agricultural implement 10. Additionally, while the illustrated embodiment shows one analyzer 34 coupled to the mounting assembly 32, it is understood that multiple analyzers 34 may be coupled to the mounting assembly 32 at various locations along the first support arm 38 and the second support arm 54. Moreover, while the analyzer 34 in the illustrated embodiment is positioned substantially perpendicular to the second support arm 54, in other embodiments the analyzer 34 may be substantially parallel to the second support arm 54, or positioned at an angle (e.g., twenty degrees, thirty degrees, forty-five degrees, etc.) relative to the second support arm 54. It will be appreciated that the orientation of the analyzer 34 may be adjusted according to the type of analyzer utilized (e.g., electrical conductivity, acoustic, chemical, etc.).

In other embodiments, the mounting assembly 32 may include a ramp to move the analyzer 34 rearwardly and proximate to the surface of the agricultural field 14. For example, the analyzer may be coupled to an analyzer member that rolls down the back of the ramp, which is coupled to the rear hitch 30. A wheel or sled may support the analyzer member against the surface of the agricultural field 14 while the analyzer 34 is positioned proximate to the surface of the agricultural field 14. The analyzer member may be coupled to the ramp via a cord and a pulley system could return the analyzer 34 and analyzer member to the ramp for storage and transportation. Moreover, in another embodiment, the analyzer 34 may be coupled to the end of a linear actuator (e.g., hydraulic cylinder). The linear actuator may include a wheel or slide configured to contact the surface of the agricultural field 14 when the actuator is extended. Extension of the actuator may move the analyzer 34 away from the agricultural implement 10 to the operation position. In a further embodiment, the mounting assembly 32 may include a single arm configured to rotate about the first axis 44. An actuator may transition the single arm between the stored position and the operation position.

Figure 5:
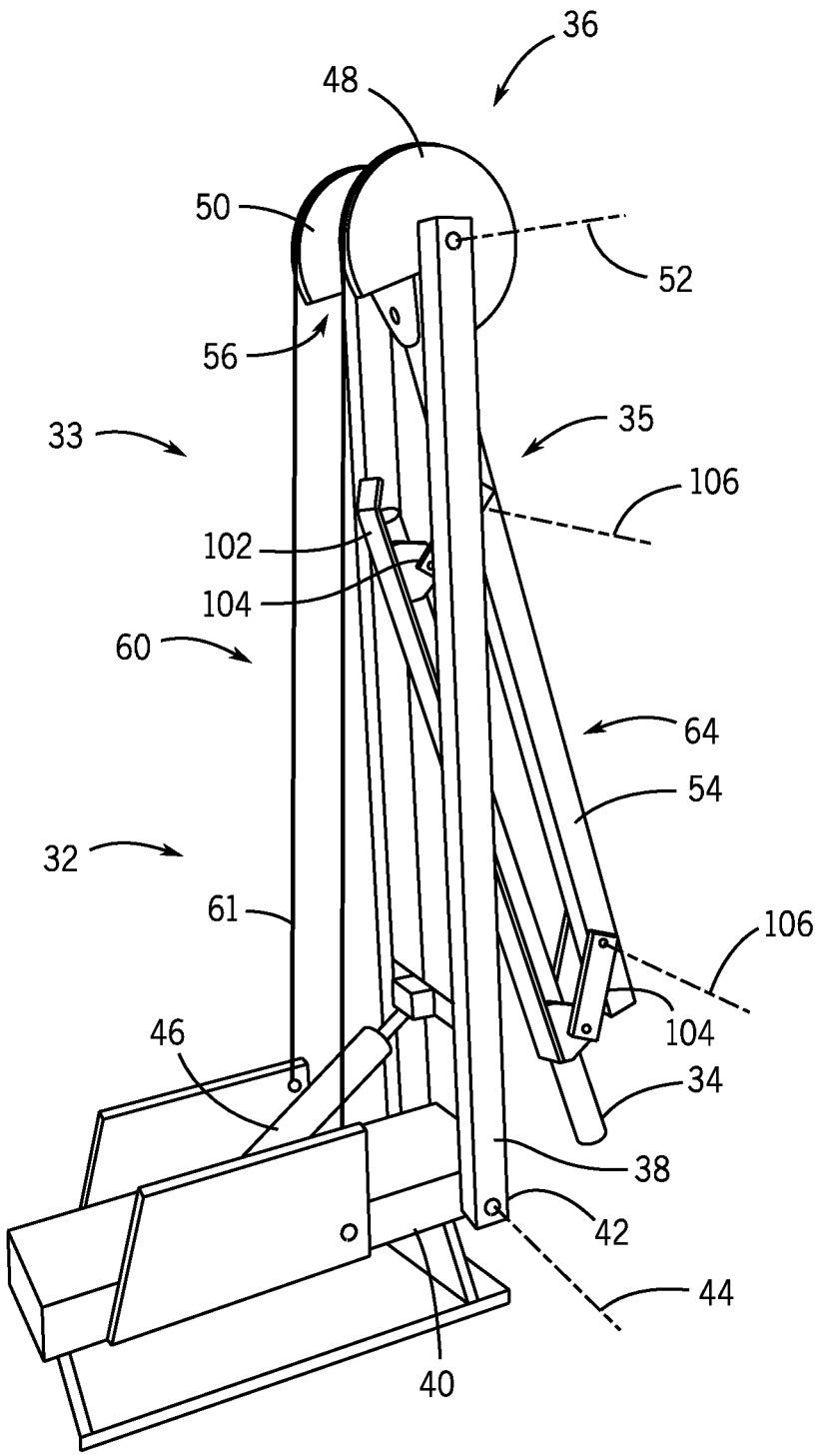
FIG. 5 is a perspective view of an embodiment of a mounting assembly that may be employed to adjust a position of an agricultural soil analyzer.

FIG. 5 is a perspective view of an embodiment of the mounting assembly 32 in the stored position 36. As described above, the mounting assembly 32 is foldable or collapsible and configured to position the analyzer 34 proximate to the surface of the agricultural field 14. The mounting assembly 32 includes a frame assembly 33 comprising frame members 35. Moreover, the first support arm 38 of the mounting assembly 32 is substantially perpendicular to the agricultural field 14 while the mounting assembly 32 is in the stored position 36. As shown, the first support arm 38 is rotatably coupled to the rear hitch 30 at the base 40. The base 40 is configured to secure the mounting assembly 32 to the rear hitch 30 or any other suitable location at the rear end of the implement 10. In the illustrated embodiment, the first support arm 38 is coupled to the base 40 at the first end 42 of the first support arm 38. As mentioned above, the mounting assembly 32 is in the stored position 36 in FIG. 5. As a result, the first support arm 38 is in a substantially vertical orientation relative to the ground. However, the first support arm 38 is configured to rotate about the first axis 44. As discussed in detail below, rotation of the first support arm 38 about the first axis 44 transitions the mounting assembly 32 between the stored position 36 and the operation position 76 in which the analyzer 34 is positioned rearward of the implement 10 and proximate to the soil surface.

As mentioned above, the first support arm 38 rotates about the first axis 44 to transition the assembly 32 between the stored position 36 and the operation position 76. In the illustrated embodiment, the actuator 46 drives the first support arm 38 to rotate about the first axis 44. As shown, the actuator 46 is a hydraulic cylinder configured to extend and retract a piston coupled to the first support arm 38 to drive rotation about the first axis 44. For example, when the piston is retracted the first support arm 38 is driven toward the stored position 36 of the assembly 32 and when the piston is extended the first support arm 38 is driven toward the operation position 76 of the assembly 32. However, it should be appreciated that alternative linear actuators (e.g., screw drives, electromechanical actuators, etc.) may be employed in alternative embodiments. In further embodiments, a rotary actuator (e.g., hydraulic, electrical, etc.) may be used. In certain embodiments, a gear and pulley system may be utilized to drive rotation of the first support arm 38. Moreover, as will be discussed in detail below, a control system may be included to control operation of the actuator 46.

In the illustrated embodiment, the mounting assembly 32 includes the rotation member 48 rotatably coupled to the first support arm 38 at the second end 50. The rotation member 48 is configured to rotate about the second axis 52. Moreover, the rotation member 48 is coupled to the second support arm 54 at the first end 56 of the second support arm 54. The second support arm 54 is configured to rotate about the second axis 52 relative to the rotation of the first support arm 38. That is, the second support arm 54 rotates about the second axis 52 with the rotation member 48. The second support arm 54 is configured to support the analyzer 34 along the length of the second support arm 54. As a result, the analyzer 34 is moved toward the position rearward of the implement and proximate to the soil surface as the first support arm 38 and the second support arm 54 are moved to the operation position 76.

In the illustrated embodiment, the actuator 60 drives the second support arm 54 to rotate about the second axis 52. As shown, the actuator 60 includes cables 61 extending from the base 40 to the rotation member 48. The cables 61 drive the rotation member 48 to rotate about the second axis 52 as the first support arm 38 rotates about the first axis 44. That is, tension in the cables 61 increases as the first support arm 38 rotates about the first axis 44, and that tension is applied to the rotation member 48 to drive the rotation member 48 to rotate about the second axis 52. As a result, the second support arm 54 also rotates about the second axis 52. The cables 61 are formed from non-electrically interactive material in the illustrated embodiment, as described in detail above. However, in alternative embodiments, the cables 61 may be straps, ropes, or any material capable of applying force to the rotation member 48 and/or the second support arm 54.

In the illustrated embodiment, a sled 102 is rotatably coupled to the second support arm 54 via a sled linkage 104. As shown, the sled linkage 104 is a parallel linkage system coupled to the second support arm 54 along the length of the second support arm 54. In certain embodiments, runners (e.g., 90 degree pieces of non-electrically interactive material) may be coupled to the sled 102 to facilitate coupling with the sled linkage 104. For example, the runners may run the length of the sled 102. The analyzer 34 is coupled to the sled 102. The sled 102 is positioned on the second support arm 54 such that the sled 102 is in the retracted position 64 while the mounting assembly 32 is in the stored position 36 and in the lowered position 72 while the mounting assembly 32 is in the operation position 76 via rotation about a sled axis 106. Accordingly, the position of the sled 102 corresponds to the position of the second support arm 54. The sled 102 is configured to distribute the weight of the second support arm 54 and the analyzer 34 while the mounting assembly 32 is in the operation position 76. That is, the sled 102 is configured to enable low disturbance positioning of the analyzer 34. Moreover, the sled 102 and the sled linkage 104 are sized to place the analyzer 34 proximate to the surface of the agricultural field 14 while the mounting assembly 32 is in the operation position 76. In the illustrated embodiment, the sled 102 and sled linkage 104 are formed from a non-electrically interactive material. Moreover, the fasteners (e.g., fasteners coupling the sled 102 to the sled linkage 104) are formed from non-electrically interactive material.

FIG. 6 is a perspective view of the mounting assembly 32 in an intermediate position between the stored position 36 and the operation position 76. In the illustrated embodiment, the first support arm 38 rotates about the first axis 44, via the actuator 46, in the first direction 66, thereby moving the second end 50 of the first support arm 38 in the longitudinal direction 68 that is opposite the direction of travel 11 of the agricultural implement 10. As the first support arm 38 rotates about the first axis 44, the second end 50 of the first support arm 38 is moved closer to the surface of the agricultural field 14. Moreover, in the illustrated embodiment, the second support arm 54 is driven to rotate about the second axis 52 in the second direction 70 by the actuator 60 (e.g., cables 61). As shown, the second direction 70 is opposite the first direction. Accordingly, rotation in the second direction 70 drives the second end 58 of the second support arm 54 to move in the direction 68. As a result, the mounting assembly 32 is elongated as the mounting assembly 32 transitions to the operation position 76, thereby moving the agricultural soil analyzer 34 rearwardly.

As mentioned above, the second support arm 54 includes the sled 102 configured to transition between the retracted position 64 while the mounting assembly 32 is in the stored position 36 and the lowered position 72 while the mounting assembly 32 is in the operation position 76. In the illustrated embodiment, the sled 102 rotates about the sled axis 106 via the sled linkage 104 as the second support arm 54 rotates about the second axis 52 in the second direction 70. The sled 102 is mounted to the second support arm 54 such that gravity pulls the sled 102 to the lowered position 72 as the mounting assembly 32 transitions to the operation position 76. Additionally, the sled 102 rotates back to the retracted position 64 as the mounting assembly 32 transitions toward the stored position 36.

FIG. 7 is a perspective view of the mounting assembly 32 in the operation position 76. As described above, the first support arm 38 is driven about the first axis 44 in the first direction 66 by the actuator 46. In the operation position 76, the first support arm 38 is substantially parallel to the surface of the agricultural field 14. Moreover, the second support arm 54 is driven about the second axis 52 in the second direction 70 by the actuator 60. As a result, the second support arm 54 is oriented substantially parallel to the surface of the agricultural field 14. Furthermore, the sled 102 contacts the surface of the agricultural field 14 to support the weight of the mounting assembly 32 in the operation position 76.

As shown, in the illustrated embodiment, the analyzer 34 is proximate to the surface of the agricultural field 14 while the mounting assembly 32 is in the operation position 76. Moreover, the analyzer 34 is substantially parallel to the second support arm 54 and the direction of travel 11. As a result, the analyzer 34 is positioned to emit and/or receive electromagnetic energy into/from the soil without contacting the surface of the agricultural field 14 while the analyzer 34 is pulled in the direction of travel 11. Furthermore, in the illustrated embodiment, the mounting assembly 32 extends in the direction 68. As illustrated, the mounting assembly 32 extends from the rear end of the implement 10 in a rearward direction relative to the direction of travel 11 of the implement 10. The extension of the mounting assembly 32 is configured to longitudinally separate the analyzer 34 from the ferrous and/or electrically interactive components of the agricultural implement 10, thereby enabling the analyzer 34 to obtain readings with improved precision due to reduced interference from the electrically interactive components. In the illustrated embodiment, the analyzer 34 is positioned approximately 8 feet rearward of the agricultural implement 10 relative to the direction of travel 11. However, in other embodiments, the analyzer 34 may be farther or closer. For example, the mounting assembly 32 may position the analyzer 34 may be between 5 feet and 20 feet from the agricultural implement 10. Moreover, the length of the sled 102 may be modified to support the mounting assembly 32 in embodiments having assemblies 32 that extend farther distances from the agricultural implement 10. Furthermore, as described above, multiple mounting assemblies 32 and analyzers 34 may be coupled to the agricultural implement 10. For example, mounting assemblies 32 may be mounted across the rear end of the agricultural implement 10.

Figure 8:
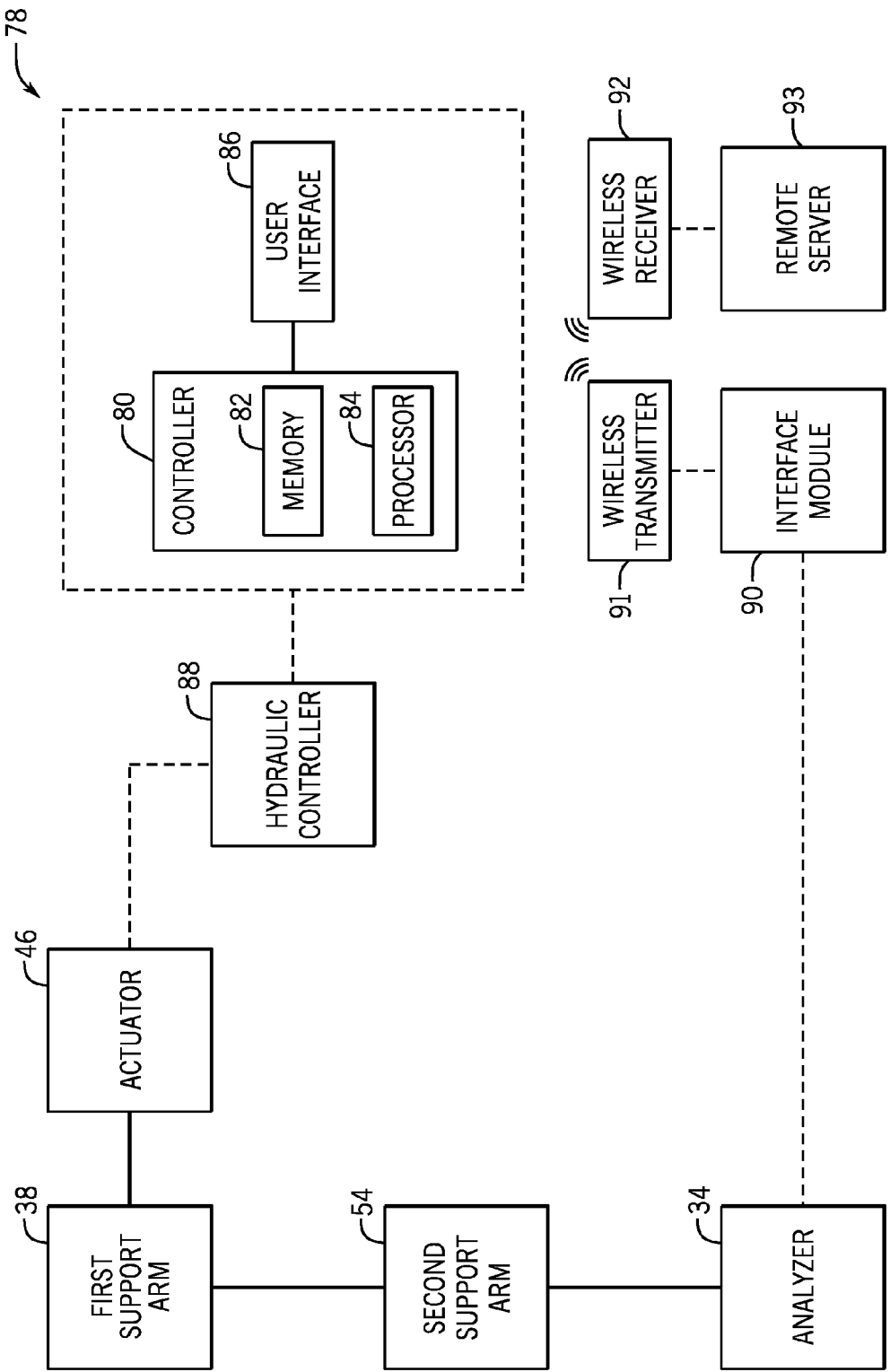
FIG. 8 is a block diagram of an embodiment of a control system for controlling the position of the mounting assembly.

FIG. 8 is a block diagram of an embodiment of a control system 78 configured to control movement of the mounting assembly 32 (e.g., between the stored position 36 and the operation position 76). In the illustrated embodiment, the control system 78 includes a controller 80 having a memory 82 and a processor 84, and a user interface 86. The memory 82 may be any type of non-transitory machine readable medium for storing data and executable instructions, such as random-access memory, read-only memory, rewritable flash memory, hard drives, optical discs, and the like. The processor 84 may execute instructions stored on the memory 82. For example, the memory 82 may contain machine readable code, such as instructions, that may be executed by the processor 84. In some embodiments, the memory 82 and processor 84 may enable automatic (e.g., processor/memory controlled) operation of the mounting assembly 32.

The operator may interact with the user interface 86 to send an operation signal to the controller 80. For example, the operator may depress a button on the user interface 86 that sends the operation signal to the controller 80 indicative of a command to drive the mounting assembly 32 into the operation position 76. As mentioned above, the processor 84 may execute instructions stored on the memory 82. The controller 80 is configured to send a control signal to a hydraulic controller 88 to drive the mounting assembly 32 to the operation position 76. For example, the hydraulic controller 88 may include a valve that controls hydraulic fluid flow to the actuator 46. Accordingly, directing the valve to open provides fluid to the actuator 46 which drives the first support arm 38 to rotate in the first direction 66 about the first axis 44. As described above, rotation of the first support arm 38 in the first direction 66 also drives rotation of the second support arm 54 in the second direction 70 via the actuator 60. Therefore, interaction with the user inference 86 may transition the mounting assembly 32 from the stored position 36 to the operation position 76. As will be appreciated, a similar operation may transition the mounting assembly 32 from the operation position 76 to the stored position 36.

As shown in FIG. 8, data acquired by the analyzer 34 is output to the interface module 90. In some embodiments, the interface module 90 includes an ISOBUS. However, in other embodiments, the interface module 90 may include a CAN-BUS, data processing software, or the like. The interface module 90 receives data from the analyzer 34. For example, in some embodiments, the analyzer 34 may perform scanning and logging operations. Then, the data is streamed into the ISOBUS of the interface module 90. In certain embodiments, the analyzer 34 may continuously (e.g., via continuous analog signals, via a continuous stream of digital data, via packets of digital data output at discrete intervals, etc.) scan/log and output the data to the interface module 90. In the illustrated embodiment, the interface module 90 is communicatively coupled to a wireless transmitter 91, which is configured to output the data to a wireless receiver 92. The wireless receiver 92 is communicatively coupled to a remote server 93, such as a memory or cloud data storage system. For example, data can be transferred via a cellular phone signal, wireless network (e.g., 3G, 4G, etc.), or the like. However, in other embodiments, the data may be transferred via wired transmitters (e.g., USB, category 5, etc.) or removable storage devices (e.g., USB memory sticks, portable hard drives, etc.). Transfer of the data to remote server 93 enables access to the data to facilitate preparation of soil maps concurrently with monitoring the soil, thereby reducing the time between data acquisition and fertilizing/planting operations. However, in other embodiments, software configured to generate three dimensional field maps may be loaded onto the memory 82, and the processor 84 may generate maps in real time/near real time during data acquisition. Accordingly, fertilizing/planting operations may be planned during data acquisition.

Figure 9:
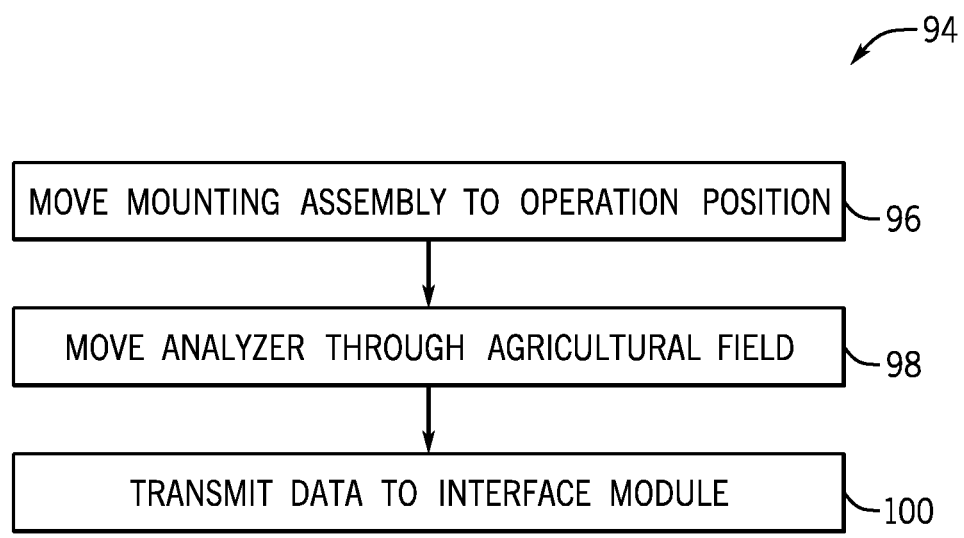
FIG. 9 is a flow chart of an embodiment of a method of for acquiring soil data using the agricultural soil analyzer of FIG. 2.

FIG. 9 is a flowchart of an embodiment of a method 94 for conducting data acquisition using the agricultural soil analyzer 34. The mounting assembly 32 is moved from the stored position 36 to the operation position 76 at block 96. For example, the actuator 46 may drive rotation of the first support arm 38 in the first direction and the actuator 60 may drive rotation of the second support arm 54 in the second direction. Moreover, in some embodiments, the control system 78 may send a signal to the actuators 46 and 60 to control rotation of the mounting assembly 32 between the stored position 36 and the operation position 76. As described above, the analyzer 34 is positioned rearward of the implement and proximate to the surface of the agricultural field 14 in the operation position 76, thereby enabling data acquisition. Moreover, while the mounting assembly 32 is in the operation position, there is sufficient distance between the analyzer 34 and the electrically interactive components of the implement 10 to enable accurate measurements. The implement 10 is moved through the agricultural field 14 while the mounting assembly 32 is in the operation position at block 98. The analyzer 34 senses and logs data while being towed through the agricultural field 14. Then, the data acquired by the analyzer 34 is transmitted to the interface module 90 at block 100. For example, the interface module 90 may transfer the data to a cloud database via the wireless transmitter 92. Or, in some embodiments, software stored on the memory 82 and processor 84 may generate yield maps based on the data acquired by the analyzer 34.

As described in detail above, the disclosed embodiments include a mounting assembly 32 configured to selectively position an agricultural soil analyzer 34 in the operation position 76, thereby positioning the agricultural soil analyzer 34 longitudinally rearward of the implement and proximate to the surface of the agricultural field 14. In certain embodiments, the mounting assembly 32 includes actuators 46 and 60 to drive the mounting assembly 32 between the stored position 36 and the operation position 76. For example, the actuator 46 may drive rotation of the first support arm 38 and the actuator 60 may drive rotation of the second support arm 54. While in the operation position 76, the analyzer 34 emits electromagnetic energy into the soil and logs the energy returned from the soil. The data obtained from the analyzer 34 is analyzed and a three dimensional soil map may be generated to direct efficient planting or fertilizing operations. Moreover, the data may be uploaded to a database (e.g., cloud based remote server) for further analysis. As a result, improvements in yields and fertilizing/planting efficiencies may be obtained.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A retractable mounting assembly, comprising:
a frame assembly comprising at least one rigid frame member, wherein the frame assembly is configured to facilitate movement of an agricultural soil analyzer from a first position longitudinally proximate to a rear end of an agricultural implement to a second position longitudinally rearward of the first position, relative to a direction of travel of the agricultural implement, the frame assembly is configured to position the agricultural soil analyzer above and proximate to a surface of an agricultural field while in the second position, and the at least one rigid frame member is formed from a non-electrically interactive material, wherein the agricultural soil analyzer is configured to monitor soil conditions of the agricultural field in the second position.

2. The retractable mounting assembly of claim 1, comprising an actuator assembly positioned proximate to the at least one rigid frame member and configured to drive the frame assembly to move the agricultural soil analyzer between the first position and the second position.

3. The retractable mounting assembly of claim 2, comprising a controller communicatively coupled to the actuator assembly, wherein the controller is configured to instruct the actuator assembly to rotate the at least one rigid frame member to move the agricultural soil analyzer between the first position and the second position.

4. The retractable mounting assembly of claim 1, wherein the agricultural soil analyzer is a non-contact electrical conductivity probe.

5. The retractable mounting assembly of claim 1, wherein the at least one frame member comprises:
a base configured to couple to the agricultural implement;
a first support arm having a first end rotatably coupled to the base and a second end, wherein the first support arm is configured to rotate about a first axis relative to the base; and
a second support arm having a first end rotatably coupled to the second end of the first support arm, and a second end configured to couple to the agricultural soil analyzer, wherein the second support arm is configured to rotate about a second axis relative to the first support arm.

6. The retractable mounting assembly of claim 5, comprising a first actuator configured to rotate the first support arm about the first axis and a second actuator configured to rotate the second support arm about the second axis.

7. The retractable mounting assembly of claim 5, comprising a support wheel rotatably coupled to the second support arm, wherein the support wheel is configured to contact the surface of the agricultural field while the agricultural soil analyzer is in the second position.

8. The retractable mounting assembly of claim 1, wherein the agricultural implement is a soil conditioner.

9. A mounting assembly for an agricultural soil analyzer, comprising:
a first support arm configured to rotatably couple to an agricultural implement, wherein the first support arm is configured to rotate about a first axis between a stored position configured to position the agricultural soil analyzer longitudinally proximate to a rear end of the agricultural implement, and an operation position configured to position the agricultural soil analyzer above and proximate to a surface of an agricultural field and longitudinally rearward of the stored position relative to a direction of travel of the agricultural implement, and the first support arm is formed from a rigid non-electrically interactive material, wherein the agricultural soil analyzer is configured to monitor soil conditions of the agricultural field in the operation position.

10. The mounting assembly of claim 9, comprising a first actuator configured to drive the first support arm to rotate between the stored position and the operation position.

11. The mounting assembly of claim 10, comprising a second actuator configured to drive a second support arm to rotate about a second axis between the stored position and the operation position, wherein the second support arm comprises a first end rotatably coupled to the first support arm and a second end coupled to the agricultural soil analyzer.

12. The mounting assembly of claim 11, comprising a support wheel rotatably coupled to the second support arm, wherein the support wheel is configured to contact the surface of the agricultural field while the second support arm is in the operation position.

13. The mounting assembly of claim 9, comprising an interface module configured to receive data acquired by the agricultural soil analyzer and to output the data to a remote server.

14. The mounting assembly of claim 13, wherein the interface module is configured to output the data via a wireless transmitter.

15. The mounting assembly of claim 13, wherein the interface module is configured to interface with a CANBUS, an ISOBUS, or a combination thereof.

16. The mounting assembly of claim 9, wherein the agricultural soil analyzer comprises a non-contact electrical conductivity probe configured to emit electromagnetic energy toward the agricultural field and to receive electromagnetic energy return from the agricultural field.

17. An agricultural soil analysis system, comprising:
- a non-contact electrical conductivity probe configured to measure electrical conductivity of soil in an agricultural field;
- a mounting assembly comprising a frame assembly coupled to the non-contact electrical conductivity probe and configured to couple to a rear end of an agricultural implement, wherein the frame assembly comprises at least one rigid frame member, and each of the at least one rigid frame members is formed from a non-electrically interactive material;
- at least one actuator configured to drive the frame assembly to transition between a first position configured to position the non-contact electrical conductivity probe longitudinally proximate to the rear end of the agricultural implement, and a second position configured to position the non-contact electrical conductivity probe above and proximate to a surface of the agricultural field and longitudinally rearward of the first position, relative to a direction of travel of the agricultural implement, wherein the non-contact electrical conductivity probe is configured to measure the electrical conductivity of soil in the agricultural field in the second position; and
- an interface module communicatively coupled to the agricultural soil analyzer and configured to communicatively couple to a control system of the agricultural implement.

18. The agricultural soil analysis system of claim 17, comprising a controller communicatively coupled to the actuator, wherein the controller is configured to instruct the at least one actuator to transition the frame assembly to the second position and to instruct the at least one actuator to transition the frame assembly to the first position.

19. The agricultural soil analysis system of claim 17, comprising a support wheel rotatably coupled to the frame assembly, wherein the support wheel is configured to contact the surface of the agricultural field while the frame assembly is in the second position.

20. The agricultural soil analysis system of claim 17, wherein the interface module comprises a wireless transmitter configured to output data acquired from the non-contact electrical conductivity probe to a remote server device.

* * * * *